(12) United States Patent
Seguin et al.

(10) Patent No.: US 9,724,242 B2
(45) Date of Patent: Aug. 8, 2017

(54) DEVICES FOR PROTECTING VULNERABLE SITES ON PATIENTS FROM LIQUID CONTAMINATION AND RELATED DEVICES, SYSTEMS, AND METHODS

(71) Applicant: Cenorin, LLC, Kent, WA (US)

(72) Inventors: Art Seguin, West Jordan, UT (US); Gerry Arambula, Seattle, WA (US)

(73) Assignee: Cenorin, LLC, Kent, WA (US)

( * ) Notice: Subject to any disclaimer, the term of this patent is extended or adjusted under 35 U.S.C. 154(b) by 407 days.

(21) Appl. No.: 14/225,268

(22) Filed: Mar. 25, 2014

(65) Prior Publication Data
US 2014/0296763 A1    Oct. 2, 2014

Related U.S. Application Data

(60) Provisional application No. 61/805,483, filed on Mar. 26, 2013.

(51) Int. Cl.
| | |
|---|---|
| *A61F 13/12* | (2006.01) |
| *A61F 13/00* | (2006.01) |
| *A61F 13/02* | (2006.01) |
| *A61B 46/20* | (2016.01) |
| *A61F 15/00* | (2006.01) |

(52) U.S. Cl.
CPC .... *A61F 13/00063* (2013.01); *A61F 13/0203* (2013.01); *A61F 13/12* (2013.01); *A61B 2046/205* (2016.02); *A61F 15/004* (2013.01); *A61F 15/008* (2013.01); *A61F 2013/00272* (2013.01)

(58) Field of Classification Search
CPC ...... A61F 13/00; A61F 13/02; A61F 13/0203; A61F 13/0206; A61F 13/12; A61F 13/122; A61F 13/128; A61F 2013/00089; A61F 2013/00165; A61F 2013/00182; A61F 15/004; A61F 15/008; A61B 46/00; A61B 46/20; A61B 2046/205
USPC .......................... 602/3, 48, 41–43; 128/888
See application file for complete search history.

(56) References Cited

U.S. PATENT DOCUMENTS

| | | | |
|---|---|---|---|
| 4,181,127 A * | 1/1980 | Linsky | A61F 13/0206 128/889 |
| 4,678,462 A | 7/1987 | Vaillancourt | |
| 4,704,177 A | 11/1987 | Vaillancourt | |

(Continued)

*Primary Examiner* — Keri J Nelson
(74) *Attorney, Agent, or Firm* — Perkins Coie LLP

(57) ABSTRACT

A protective device configured in accordance with a particular embodiment includes a cover including a first region that extends over a vulnerable site on a patient and a second region that extends over an area on the patient peripheral to the vulnerable site. The first region of the cover is at least generally impermeable to liquid water. The device further includes an adhesive film and a liquid-absorbing element. The adhesive film is configured to form an adhesive bond between the second region of the cover and the patient. The bond has an inner edge portion positioned toward the vulnerable site and an outer edge portion positioned away from the vulnerable site. The liquid-absorbing element is configured to absorb liquid contamination at the outer edge portion of the bond and/or liquid contamination approaching the outer edge portion of the bond when the cover is operably positioned on the patient.

7 Claims, 20 Drawing Sheets

(56) References Cited

U.S. PATENT DOCUMENTS

| | | | |
|---|---|---|---|
| 4,917,112 A * | 4/1990 | Kalt | A61F 13/023 128/888 |
| 5,074,847 A | 12/1991 | Greenwell et al. | |
| 5,080,108 A | 1/1992 | Roth | |
| 5,092,323 A * | 3/1992 | Riedel | A61F 13/023 128/888 |
| 5,116,324 A | 5/1992 | Brierley et al. | |
| 5,188,608 A | 2/1993 | Fritts | |
| 5,230,350 A * | 7/1993 | Fentress | A61F 15/008 128/846 |
| 5,372,589 A | 12/1994 | Davis | |
| 5,449,349 A | 9/1995 | Sallee et al. | |
| 5,531,695 A | 7/1996 | Swisher | |
| 5,562,107 A * | 10/1996 | Lavender | A61F 13/0269 128/888 |
| 5,832,928 A | 11/1998 | Padilla, Jr. | |
| 6,222,090 B1 | 4/2001 | Weston | |
| 6,257,240 B1 | 7/2001 | Shesol | |
| 6,267,115 B1 | 7/2001 | Marshel | |
| 6,273,873 B1 | 8/2001 | Fleischer | |
| 6,315,759 B1 | 11/2001 | Peterson | |
| 6,528,697 B1 * | 3/2003 | Knutson | A61F 13/02 602/42 |
| 6,809,230 B2 | 10/2004 | Hancock et al. | |
| 6,893,422 B2 | 5/2005 | Altman | |
| 7,723,561 B2 | 5/2010 | Propp | |
| 7,913,320 B2 | 3/2011 | Grissom | |
| 8,197,447 B2 | 6/2012 | Wright | |
| 8,834,426 B2 | 9/2014 | Shipman | |
| 8,858,505 B1 | 10/2014 | Justus et al. | |
| 8,859,838 B1 | 10/2014 | Nelson et al. | |
| 8,882,718 B2 | 11/2014 | Mullet et al. | |
| 2003/0055382 A1 | 3/2003 | Schaeffer | |
| 2004/0204685 A1 | 10/2004 | Wright et al. | |
| 2005/0020977 A1 | 1/2005 | Eldridge et al. | |
| 2005/0027227 A1 * | 2/2005 | Dumas | A61F 15/004 602/41 |
| 2006/0084904 A1 | 4/2006 | Ritchey | |
| 2008/0208130 A1 | 8/2008 | Furman | |
| 2009/0247965 A1 | 10/2009 | Williams | |
| 2010/0100049 A1 | 4/2010 | Godfrey | |
| 2011/0040258 A1 | 2/2011 | Robison | |
| 2011/0087144 A1 | 4/2011 | Lee et al. | |
| 2012/0277648 A1 * | 11/2012 | Kendall | A61F 13/025 602/55 |
| 2013/0110048 A1 | 5/2013 | Herzog | |
| 2014/0100533 A1 | 4/2014 | Lyons | |
| 2014/0180257 A1 | 6/2014 | Zinn | |
| 2015/0257833 A1 | 9/2015 | Dabel | |
| 2015/0290449 A1 | 10/2015 | Yanik | |
| 2015/0367119 A1 | 12/2015 | Stillson | |
| 2016/0067106 A1 | 3/2016 | Howell et al. | |
| 2016/0166806 A1 | 6/2016 | Scheremet et al. | |

* cited by examiner

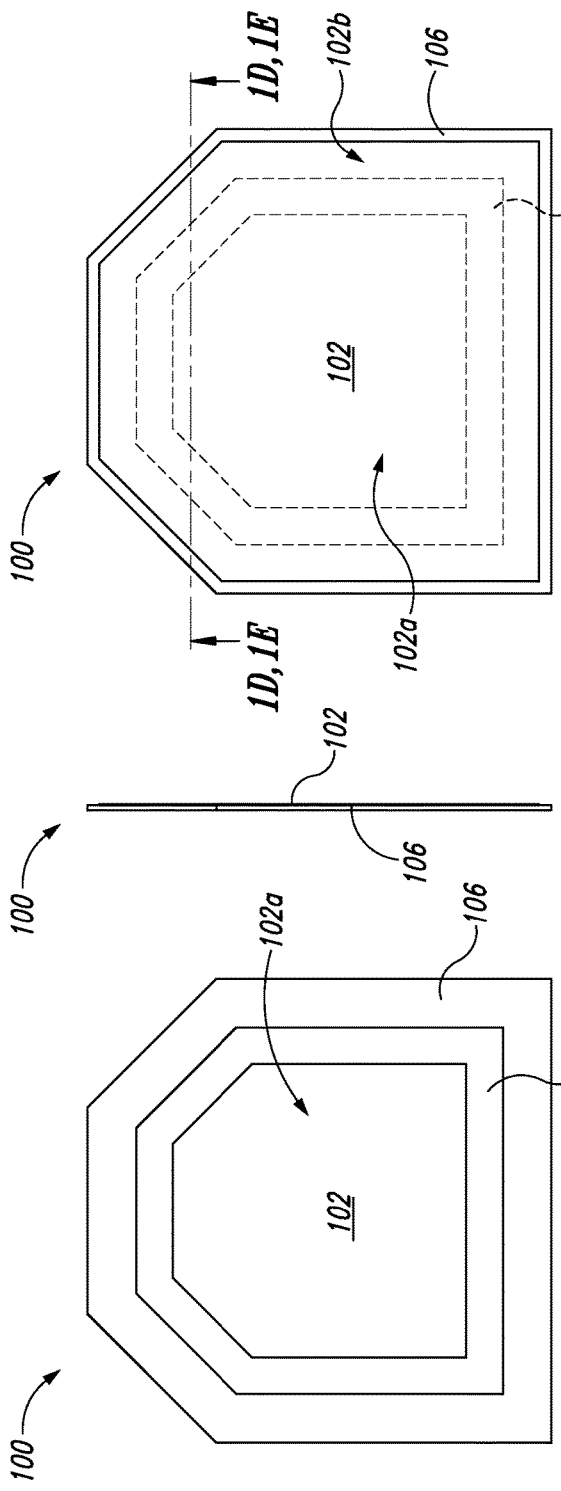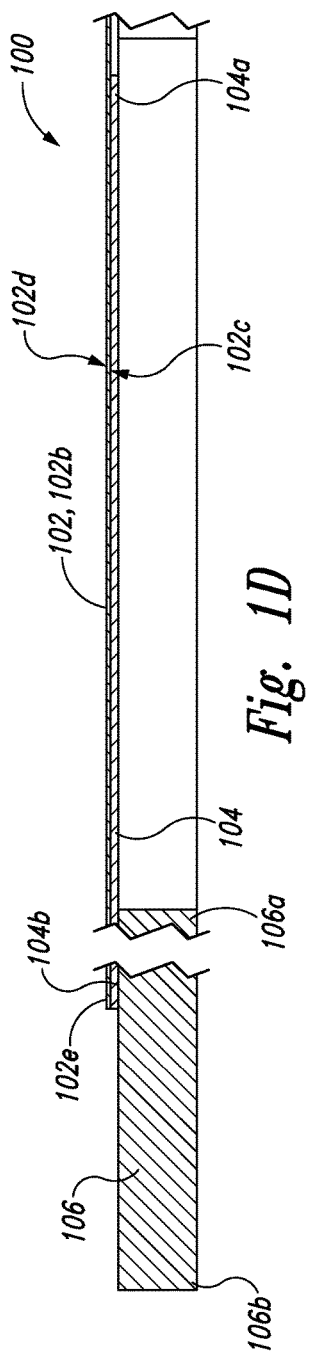

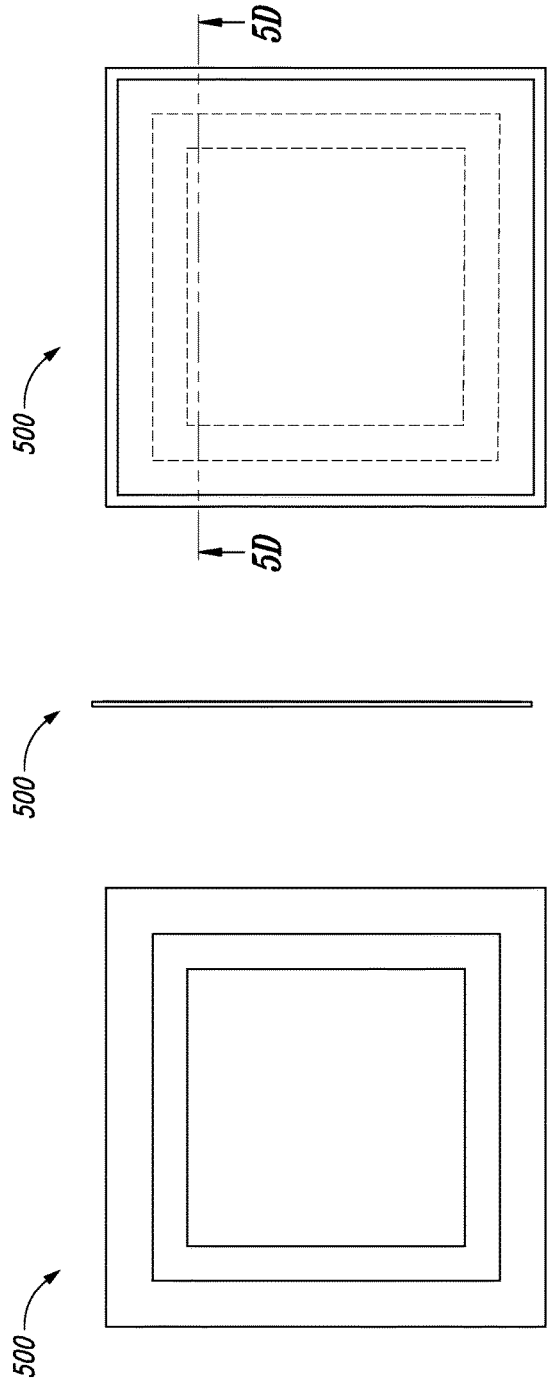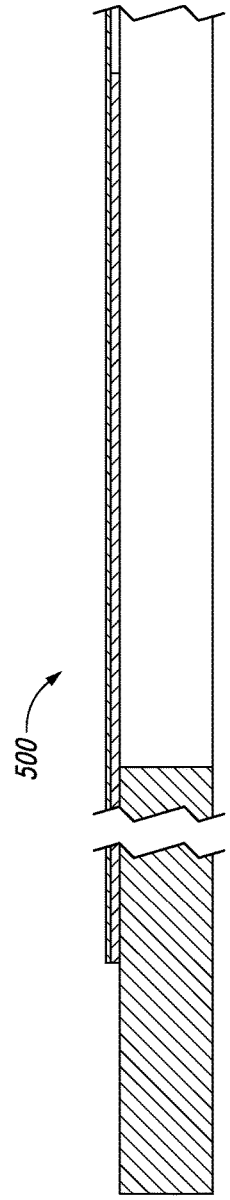
Fig. 5A  Fig. 5B  Fig. 5C  Fig. 5D

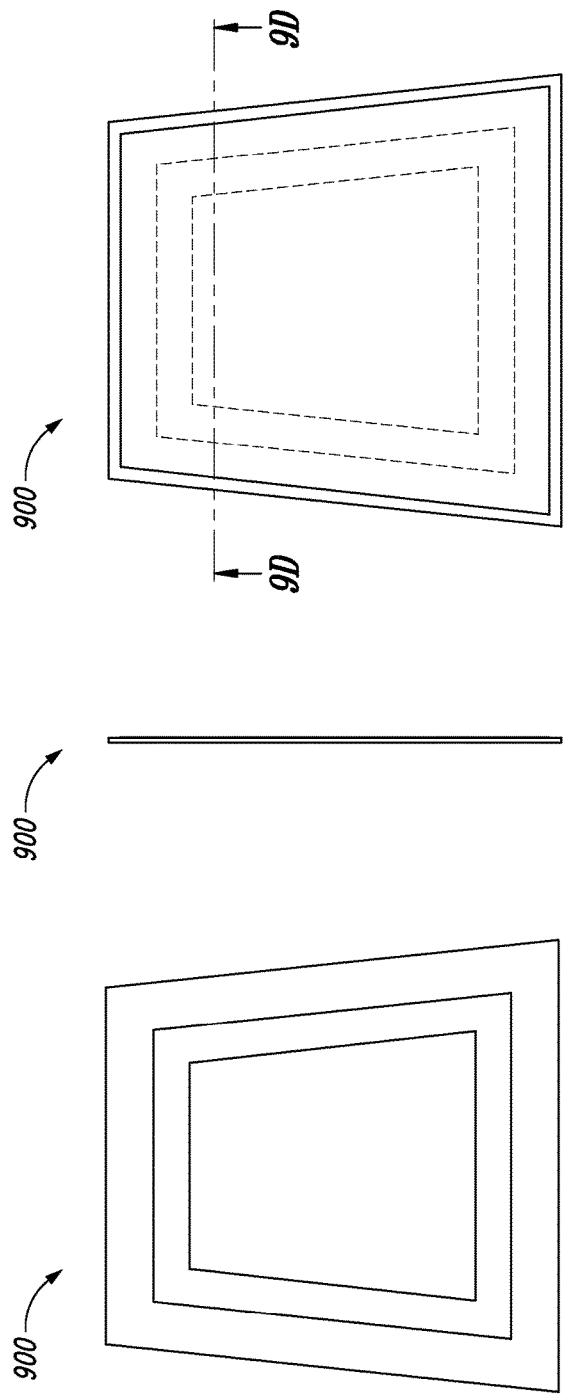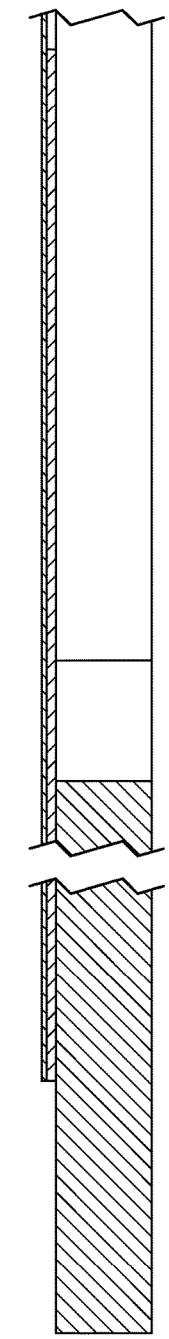

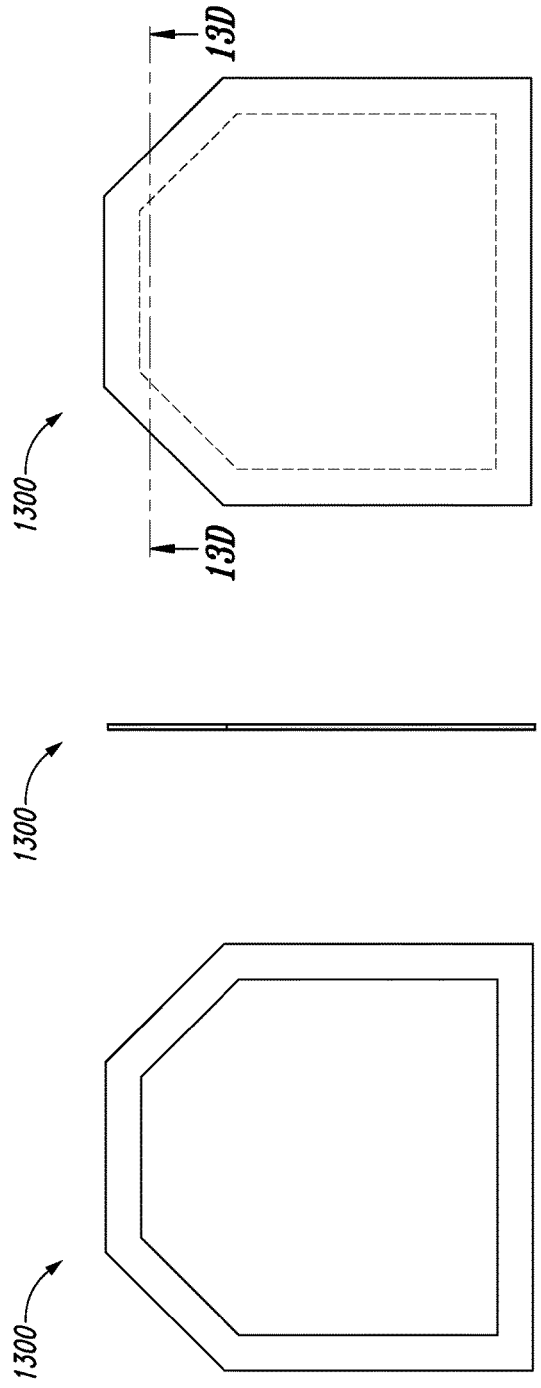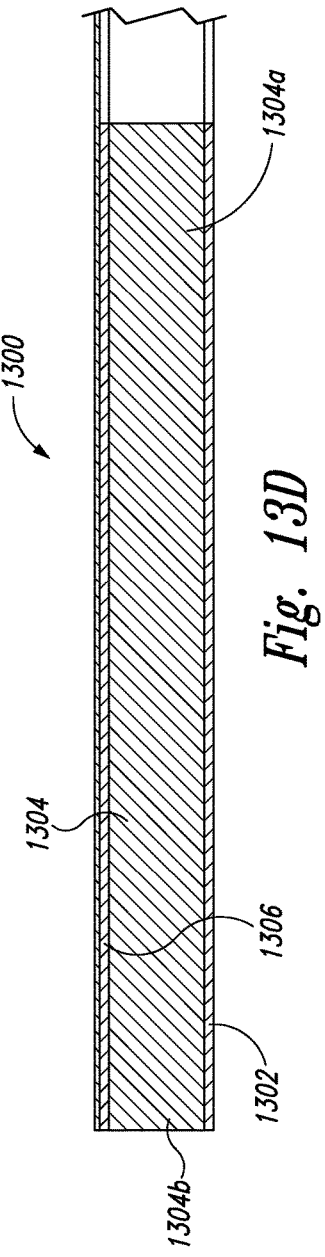
Fig. 13A  Fig. 13B  Fig. 13C  Fig. 13D

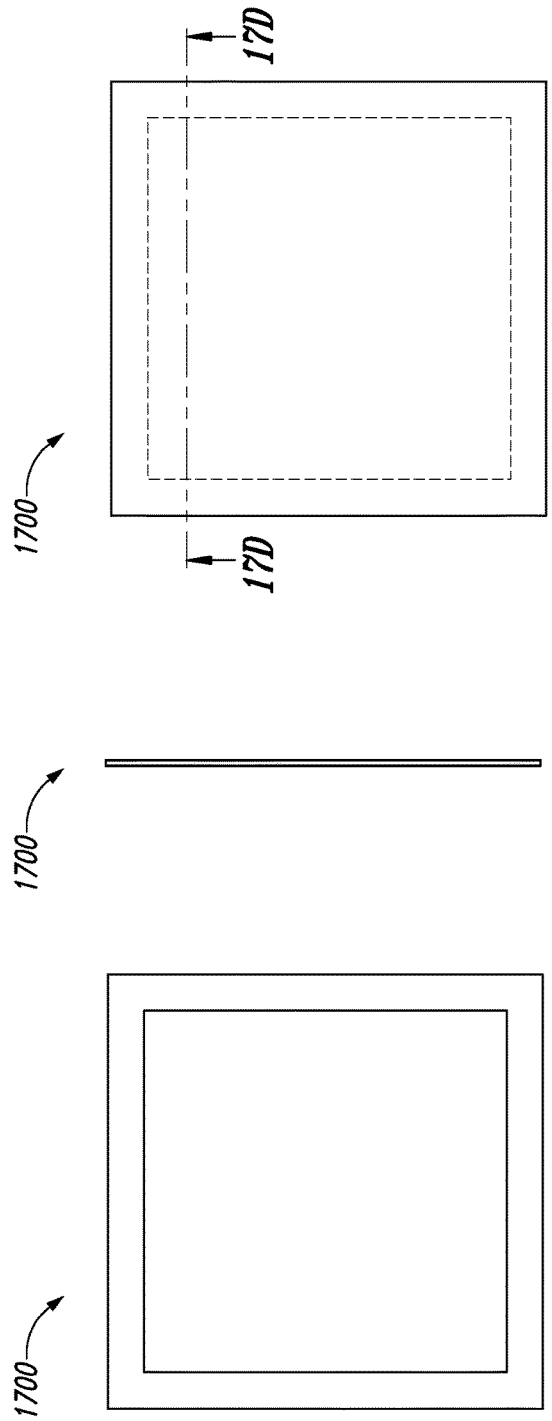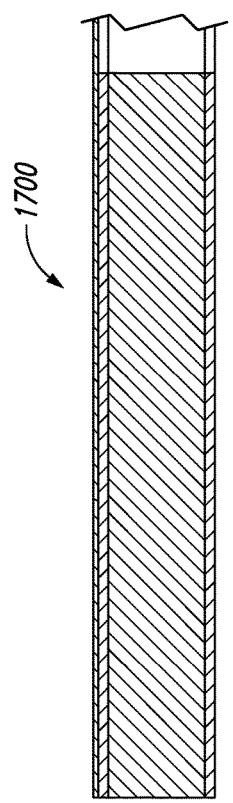
Fig. 17A
Fig. 17B
Fig. 17C
Fig. 17D

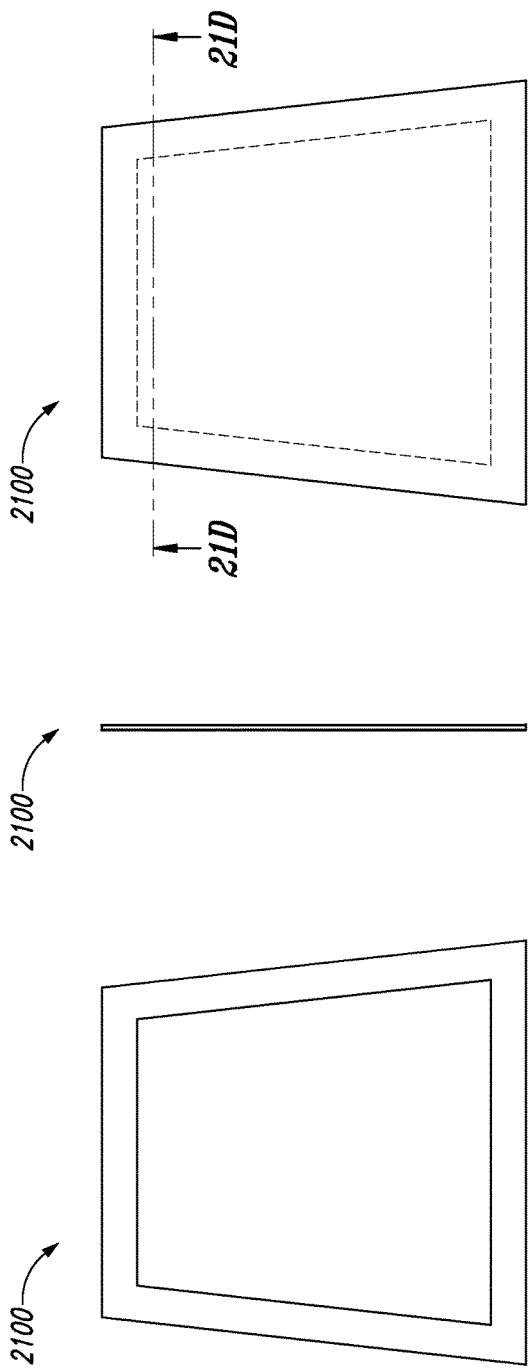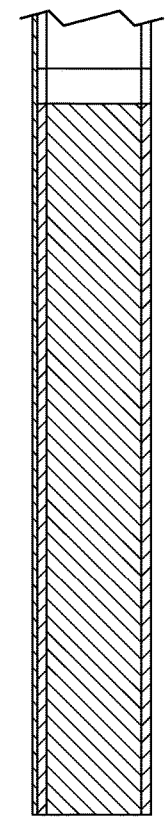

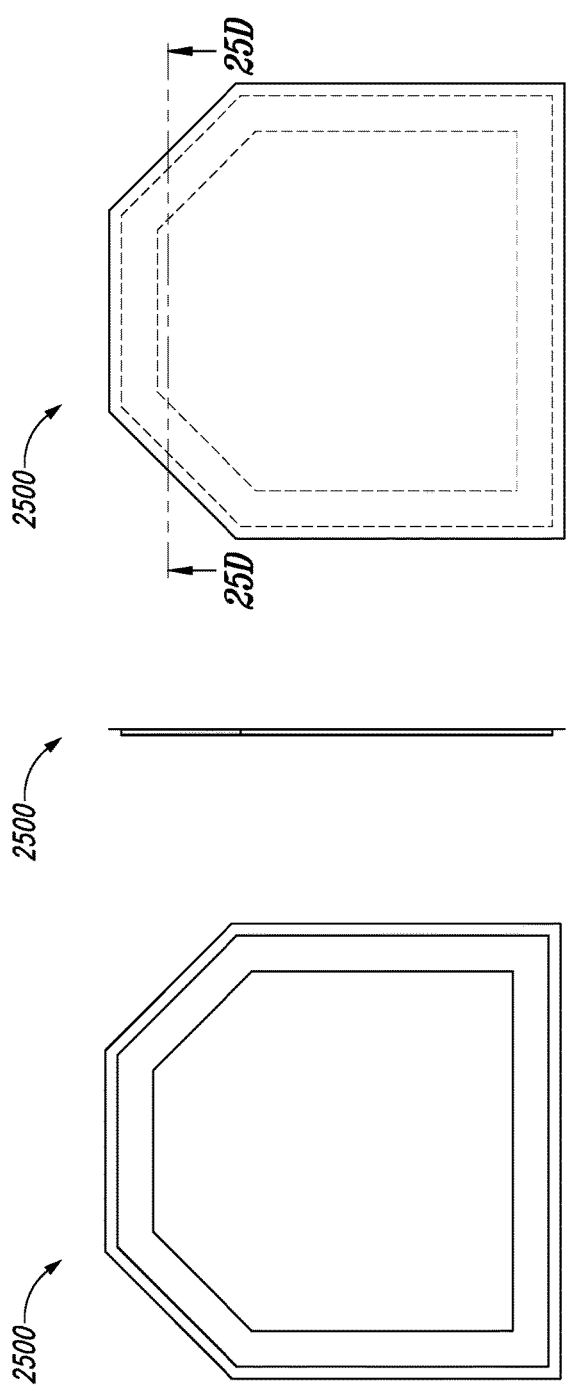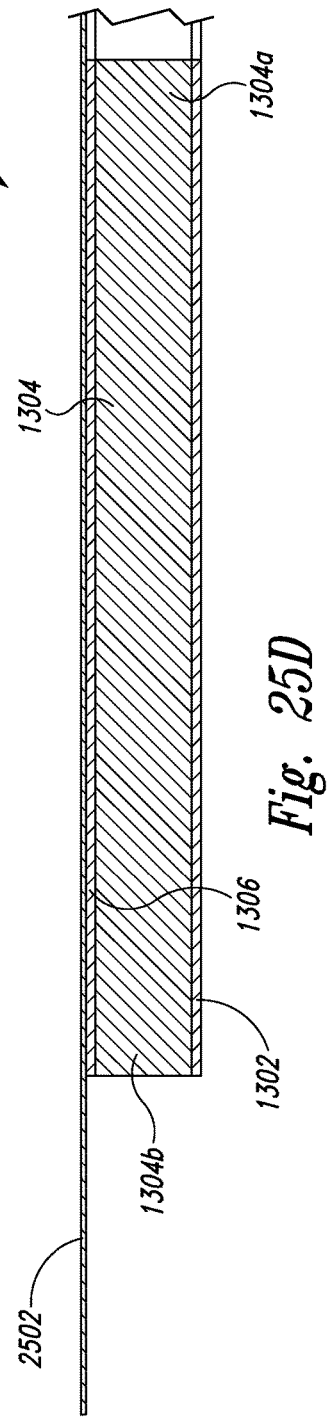
Fig. 25A
Fig. 25B
Fig. 25C
Fig. 25D

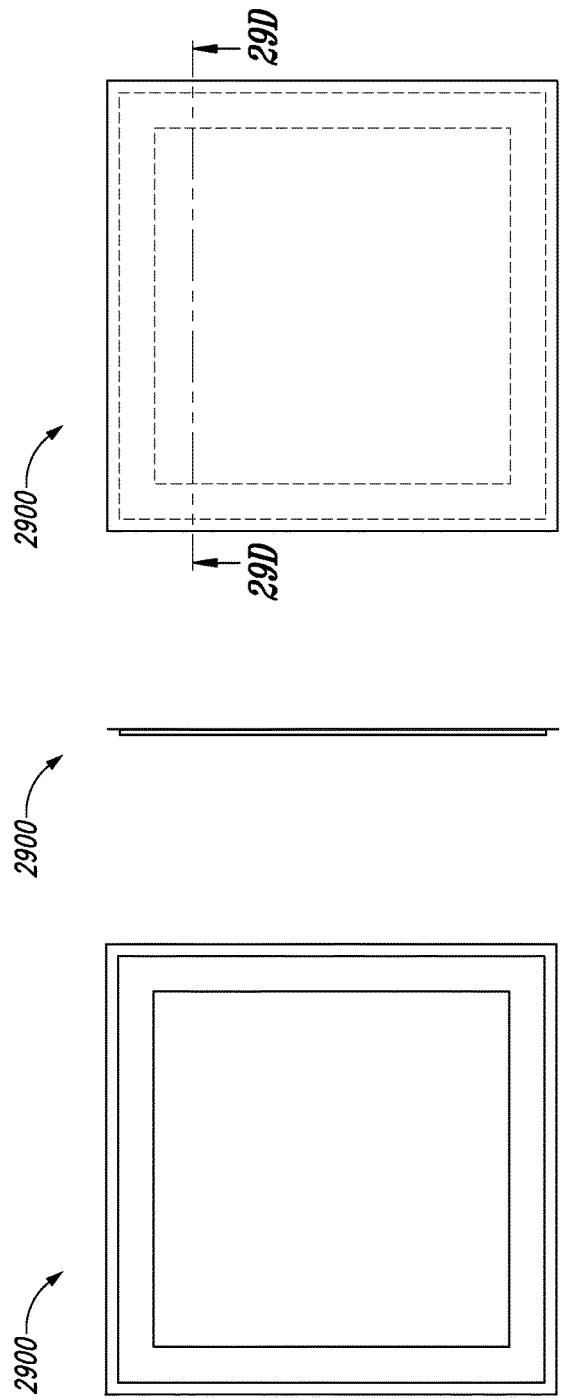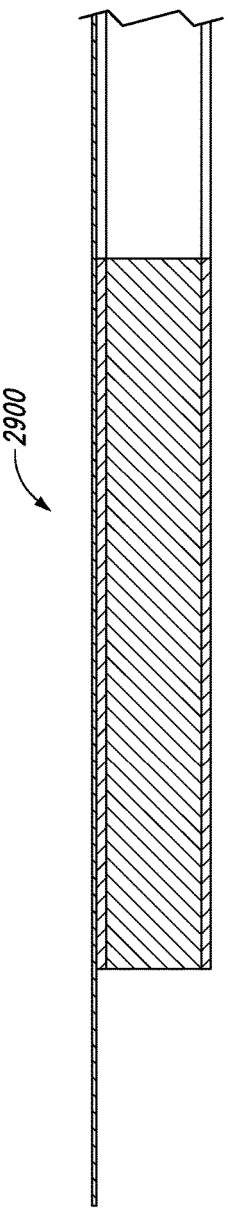
Fig. 29A  Fig. 29B  Fig. 29C  Fig. 29D

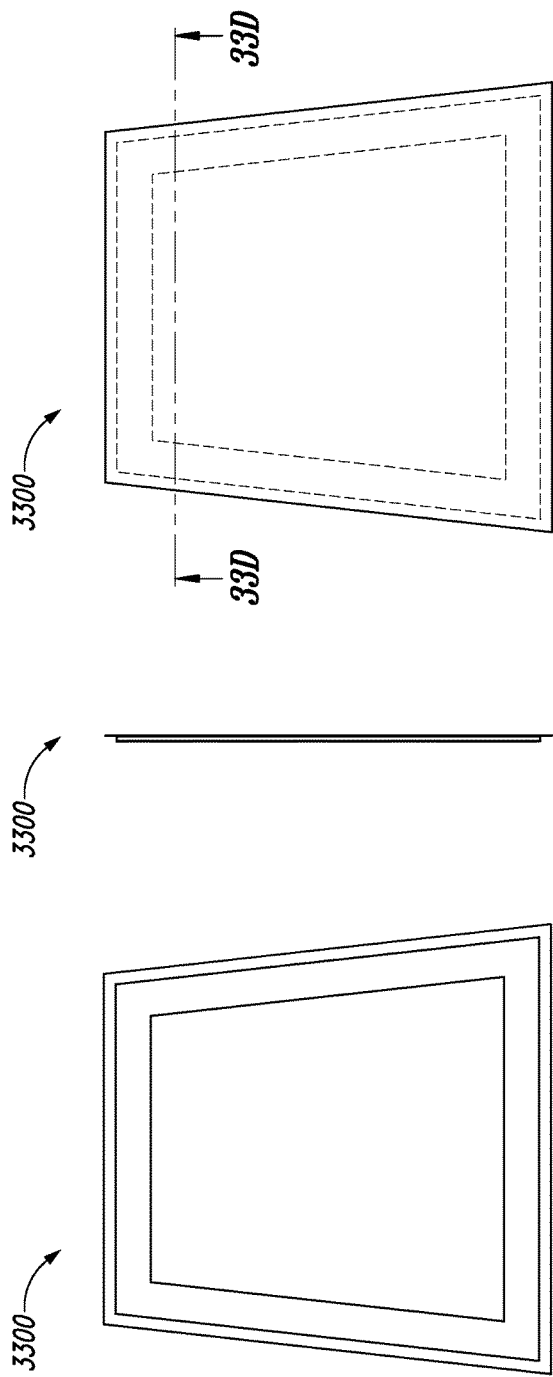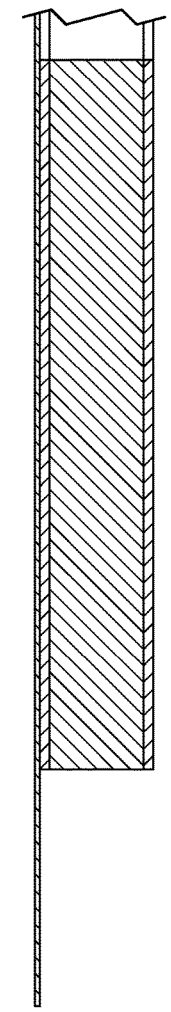
Fig. 33A    Fig. 33B    Fig. 33C    Fig. 33D

DEVICES FOR PROTECTING VULNERABLE SITES ON PATIENTS FROM LIQUID CONTAMINATION AND RELATED DEVICES, SYSTEMS, AND METHODS

CROSS-REFERENCE TO RELATED APPLICATIONS

This application claims the benefit of the earlier filing date of U.S. Provisional Application No. 61/805,483, filed Mar. 26, 2013, which is incorporated herein by reference in its entirety.

TECHNICAL FIELD

The present technology is related to protective devices for medical applications. In particular, at least some embodiments are related to devices for protecting vulnerable sites (e.g., percutaneous sites) on patients from respiratory exudates and/or other types of liquid contamination.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

FIGS. 1A, 1B, and 1C are a front (i.e., skin-contact) side view, an edge view, and a back view, respectively, of a protective device configured in accordance with an embodiment of the present technology.

FIG. 1D is a cross-sectional end view of the protective device shown in FIGS. 1A-1C taken along the line 1D-1D in FIG. 1C in a non-deployed state.

FIGS. 5A, 5B, and 5C are a front (i.e., skin-contact) side view, an edge view, and a back view, respectively, of a protective device configured in accordance with an embodiment of the present technology.

FIG. 5D is a cross-sectional end view of the protective device shown in FIGS. 5A-5C taken along the line 5D-5D in FIG. 5C.

FIGS. 9A, 9B, and 9C are a front (i.e., skin-contact) side view, an edge view, and a back view, respectively, of a protective device configured in accordance with an embodiment of the present technology.

FIG. 9D is a cross-sectional end view of the protective device shown in FIGS. 9A-9C taken along the line 9D-9D in FIG. 9C.

FIGS. 13A, 13B, and 13C are a front (i.e., skin-contact) side view, an edge view, and a back view, respectively, of a protective device configured in accordance with an embodiment of the present technology.

FIG. 13D is a cross-sectional end view of the protective device shown in FIGS. 13A-13C taken along the line 13D-13D in FIG. 13C.

FIGS. 17A, 17B, and 17C are a front (i.e., skin-contact) side view, an edge view, and a back view, respectively, of a protective device configured in accordance with an embodiment of the present technology.

FIG. 17D is a cross-sectional end view of the protective device shown in FIGS. 17A-17C taken along the line 17D-17D in FIG. 17C.

FIGS. 21A, 21B, and 21C are a front (i.e., skin-contact) side view, an edge view, and a back view, respectively, of a protective device configured in accordance with an embodiment of the present technology.

FIG. 21D is a cross-sectional end view of the protective device shown in FIGS. 21A-21C taken along the line 21D-21D in FIG. 21C.

FIGS. 25A, 25B, and 25C are a front (i.e., skin-contact) side view, an edge view, and a back view, respectively, of a protective device configured in accordance with an embodiment of the present technology.

FIG. 25D is a cross-sectional end view of the protective device shown in FIGS. 25A-25C taken along the line 25D-25D in FIG. 25C.

FIGS. 29A, 29B, and 29C are a front (i.e., skin-contact) side view, an edge view, and a back view, respectively, of a protective device configured in accordance with an embodiment of the present technology.

FIG. 29D is a cross-sectional end view of the protective device shown in FIGS. 29A-29C taken along the line 29D-29D in FIG. 29C.

FIGS. 33A, 33B, and 33C are a front (i.e., skin-contact) side view, an edge view, and a back view, respectively, of a protective device configured in accordance with an embodiment of the present technology.

FIG. 33D is a cross-sectional end view of the protective device shown in FIGS. 33A-33C taken along the line 33D-33D in FIG. 33C.

DETAILED DESCRIPTION

Figure 1E:
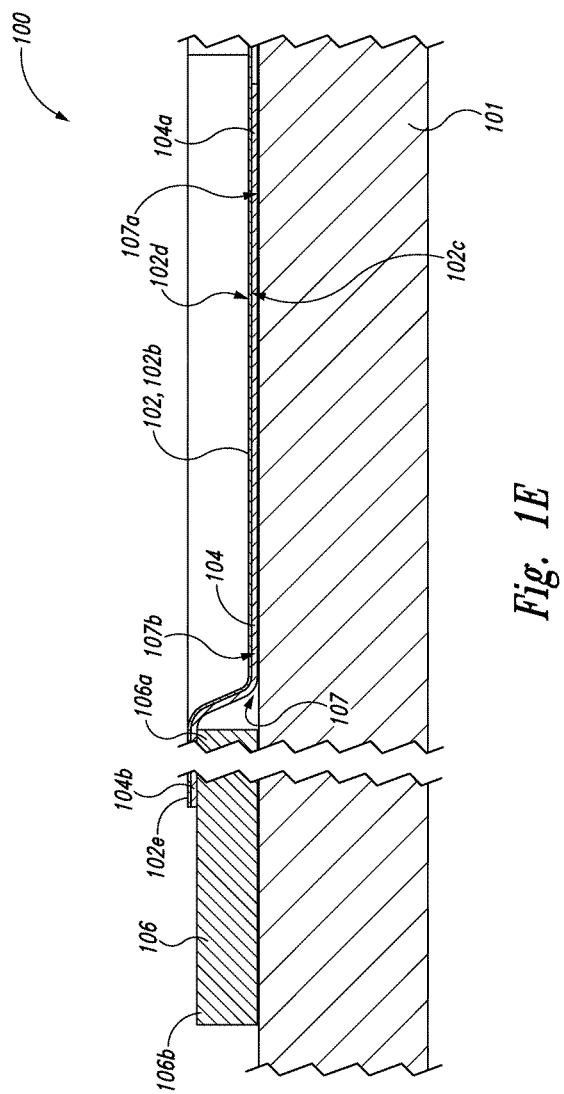
FIG. 1E is a cross-sectional end view of the protective device shown in FIGS. 1A-1C taken along the line 1E-1E in FIG. 1C in a deployed state against a patient's skin.

Specific details of several embodiments of the present technology are described herein with reference to FIGS. 1A-37. It should be noted that other embodiments in addition to those disclosed herein are within the scope of the present technology. For example, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

It is typically advantageous to maintain certain types of vulnerable sites at least generally free of liquid contamination. For example, it can be advantageous to prevent or reduce exposure of a percutaneous site or a wound to respiratory exudates and/or other types of liquid contamination that can cause an infection at the site. Since percutaneous sites, wounds, and other types of vulnerable sites may remain open and/or otherwise vulnerable for relatively long periods of time (e.g., many days, weeks, or longer), maintaining the sites at least generally free of liquid contamination can be challenging. As one example, a vulnerable site on a patient's neck or otherwise near a patient's head may be exposed to sputum, mucus, saliva, and/or other respiratory exudates and bodily secretions. As another example, a vulnerable site on a patient's torso or limb may be exposed to sweat, bathing runoff (e.g., from a sponge bath), spilled fluids, and/or other types of liquid contamination. Conventional dressings typically are ill suited for protecting vulnerable sites from liquid contamination. For example, many conventional dressings are designed primarily to reduce or prevent egress of liquid exudates (e.g., blood) from a wound, not to protect the wound from external sources of liquid contamination. To the extent that these and other conventional dressings may absorb liquid contamination, the absorbed liquid contamination typically is held in sustained contact with an adhesive and/or with the patient's skin. This can cause irritation, adhesive failure, and/or inadequate ventilation and/or have other undesirable consequences. For example, enzymes in saliva can accelerate the breakdown of skin, thereby causing conventional dressings adhesively attached to skin to detach prematurely and/or contaminating a wound site.

Protective devices, systems, and methods configured in accordance with at least some embodiments of the present technology can at least partially overcome one or more of the disadvantages and technical challenges discussed above and/or one or more other disadvantages and/or technical challenges associated with conventional protective devices, systems, and methods. For example, a protective device configured in accordance with a particular embodiment includes a liquid-impermeable cover configured to extend over a vulnerable site on a patient and a liquid-absorbing element configured to absorb liquid contamination at and/or approaching an outer edge portion of an adhesive bond between the cover and the patient's skin. The liquid-absorbing element can hold the liquid contamination away from the vulnerable site and the cover can act as a complete or partial barrier to liquid contamination not held by the liquid-absorbing element. Furthermore, the liquid-absorbing element can help to protect the adhesive bond from degrading in the presence of liquid contamination. A variety of other advantages in addition to or instead of these advantages are also possible.

Selected Examples of Protective Devices

FIGS. 1A, 1B, and 1C are a front (i.e., skin-contact) side view, an edge view, and a back view, respectively, of a protective device 100 configured in accordance with an embodiment of the present technology. FIG. 1D is a cross-sectional end view of the protective device 100 taken along the line 1D-1D in FIG. 1C in a non-deployed state. FIG. 1E is a cross-sectional end view of the protective device 100 taken along the line 1E-1E in FIG. 1C in a deployed state against a patient's skin 101. With reference to FIGS. 1A-1E together, the protective device 100 can include a cover 102, an adhesive film 104, and a liquid-absorbing element 106. The cover 102 can have a first (e.g., central) region 102a and a second (e.g., peripheral) region 102b extending around a perimeter of the first region 102a. The cover 102 can be configured to be operably positioned on a human patient such that the first region 102a extends over a vulnerable site (not shown) on the patient and the second region 102b extends over an area on the patient peripheral to the vulnerable site. In some embodiments, the cover 102 is flexible and configured to drape over a vulnerable site, such as to accommodate the dimensionality of a percutaneous device (e.g., a peripheral cannula extending into a patient's vasculature). For example, the first region 102a can be a region of a sheet of flexible polymeric material, such as flexible polyurethane, flexible polyethylene, or another suitable flexible polymeric material. In other embodiments, the cover 102 can be less flexible. For example, the first region 102a can be a region of a three-dimensional shell that is at least generally rigid and configured to at least partially encase a three-dimensional space adjacent to a vulnerable site. Furthermore, the first region 102a can be opaque, transparent (e.g., to allow a vulnerable site or a percutaneous device at a vulnerable site to be visually monitored), or otherwise translucent.

The protective device 100 can be configured to protect the vulnerable site from liquid (e.g., non-aerosolized liquid and aerosolized liquid) and particulate contamination. For example, the first region 102a, the second region 102b, or both can be at least generally impermeable to liquid water. In a particular example, the protective device 100 protects a percutaneous device (not shown) that is positioned at least proximate to a patient's neck and the protective device 100 reduces the probability that an infection will develop at the vulnerable site by protecting the vulnerable site from respiratory exudates (e.g., sputum, mucus, and/or saliva) and other sources of contamination. In other examples, the protective device 100 can be used at other suitable anatomical locations. Furthermore, the protective device 100 can be used to protect a vulnerable site that does not include a percutaneous device, such as a dressed wound, an undressed wound, or a stoma without an associated percutaneous device. Still further, the protective device 100 can be used to protect a vulnerable site from liquid contamination other than respiratory exudates, such as sweat, bathing runoff, or spilled liquids. Still further, in addition to or instead of reducing the probability that an infection will develop at a vulnerable site, the protective device 100 can address a different type of vulnerability, such as susceptibility to shifting of a percutaneous device relative to a patient, susceptibility to inadvertent scratching, or another suitable type of vulnerability.

When operably positioned on a patient, the cover 102 and components of the cover 102 individually can have first side 102c facing toward the patient and a second side 102d facing away from the patient. Furthermore, the cover 102 can have an outer edge portion 102e extending between the first and second sides 102c, 102d. The adhesive film 104 can be attached to the cover 102 directly or indirectly and can have an inner edge portion 104a toward the first region 102a and an outer edge portion 104b away from the first region 102a. For example, the adhesive film 104 can be disposed along the first side 102c of the second region 102b of the cover 102. The adhesive film 104 can be configured to form an adhesive bond 107 (FIG. 1E) between the second region 102b and the patient's skin 101. The bond 107 can have an inner edge portion 107a positioned toward a vulnerable site and an outer edge portion 107b positioned away from the vulnerable site.

The bond 107 can be a direct bond between the second region 102b and the patient or an indirect bond. Furthermore, in some embodiments, the outer edge portion 107b of the bond 107 is aligned with the outer edge portion 102e of the cover 102. In other embodiments, the outer edge portion 107b of the bond 107 can be inset (e.g., toward the vulnerable site) relative to the outer edge portion 102e of the cover 102. For example, the adhesive film 104 can be configured such that the outer edge portion 102e of the cover 102 is positioned at least about 0.5 centimeter or at least another suitable distance further from the vulnerable site than the outer edge portion 107b of the bond 107 when the cover 102 is operably positioned on a patient. In some embodiments, the bond 107 at least generally blocks direct air exchange between the vulnerable site and the liquid-absorbing element 106. This can be useful, for example, to enhance separation between the vulnerable site and liquid contaminants within the liquid-absorbing element 106. In other embodiments, the vulnerable site can be open to air exchange with the liquid-absorbing element 106. For example, the bond 107 can be between the liquid-absorbing element 106 and the patient's skin 101 and the cover 102 can be attached to the patient via both the liquid-absorbing element 106 and the bond 107 rather than via the bond 107 only.

The adhesive film 104 can extend around all or a portion of the perimeter of the first region 102a. In some embodiments, the cover 102 includes a third region (not shown) at a portion of the perimeter of the first region 102a along which the adhesive film 104 does not extend. For example, the adhesive film 104 can extend around a percentage of the perimeter of the first region 102a of the cover 102 from about 5% to about 95%, from about 10% to about 95%, from about 15% to about 95%, or within another suitable range. The third region can be configured to allow ventilation of a vulnerable site when the cover 102 is operably positioned on a patient. Such ventilation, for example, can reduce or prevent undue condensation on the first side 102c of the cover 102 even when the first region 102a of the cover 102 is impermeable to water vapor. In embodiments, the adhesive film 104 can extend around the entire perimeter of the first region 102a. In these and other embodiments, the first region 102a of the cover 102 can be permeable to water vapor, the cover 102 can be configured to allow ventilation in another suitable manner, or the cover 102 can be configured to leave a vulnerable site unventilated. In a particular example of ventilation, the cover 102, the adhesive film 104, or another suitable component of the device 100 includes an active or passive vent (not shown), such as a perforation, a fenestration, a filtered opening, or a baffled opening. The vent, for example, can be configured to allow water vapor to escape from the vulnerable site without unduly interfering with the ability of the cover 102 to exclude liquid contamination from the vulnerable site.

The liquid-absorbing element 106 can be attached to the cover 102 directly or indirectly. In some embodiments, at least a portion of the liquid-absorbing element 106 is disposed along the second side 102d of the cover 102 (e.g., along the second side 102d of the second region 102b of the cover 102) such that the cover 102 is positioned between at least a portion of the liquid-absorbing element 106 and a patient when the cover 102 is operably positioned on the patient. In other embodiments, the liquid-absorbing element 106 can be disposed along the first side 102c of the cover 102, such that at least a portion of the liquid-absorbing element 106 is positioned between the cover 102 and a patient when the cover 102 is operably positioned on the patient. In sill other embodiments, the liquid-absorbing element 106 can be disposed partially along the first side 102c of the cover 102 and partially along the second side 102d of the cover 102. The position of the liquid-absorbing element 106 relative to the cover 102 can affect how liquid contamination within the liquid-absorbing element 106 is held. For example, positioning the liquid-absorbing element 106 between the cover 102 and the patient can, in at least some cases, enhance separation between the liquid contamination and the bond 107. Alternatively, positioning the cover 102 between the liquid-absorbing element 106 and the patient can, in at least some cases, enhance separation between the liquid contamination and the patient's skin 101 and/or accelerate evaporation of the liquid contamination, such as by exposing a relatively large portion of the liquid-absorbing element 106 to the atmosphere.

The liquid-absorbing element 106 can be configured to absorb liquid contamination at the outer edge portion 107b of the bond 107 and/or liquid contamination approaching the outer edge portion 107b of the bond 107 when the cover 102 is operably positioned on a patient. For example, the liquid-absorbing element 106 can be configured to wick liquid contamination away from the outer edge portion 107b of the bond 107. The liquid-absorbing element 106 can have an inner edge portion 106a positioned toward the bond 107 and an outer edge portion 106b positioned away from the bond 107. As shown in FIGS. 1A-1E, at least a portion of the liquid-absorbing element 106 can be positioned further from the vulnerable site than the outer edge portion 107b of the bond 107 when the cover 102 is operably positioned on the patient. Furthermore, in some embodiments, the outer edge portion 102e of the cover 102 can be positioned closer to the vulnerable site than the outer edge portion 106b of the liquid-absorbing element 106. In other embodiments, the outer edge portion 102e of the cover 102 can be positioned further from the vulnerable site than the outer edge portion 106b of the liquid-absorbing element 106. For example, the outer edge portion 102e of the cover 102 can be configured to drape over the outer edge portion 106b of the liquid-absorbing element 106 when the cover 102 is operably positioned on the patient.

The liquid-absorbing element 106 can be an elongate strip of absorbent material or have another suitable form. The liquid-absorbing element 106 can have an average dimension (e.g., thickness) perpendicular to an associated skin surface greater than about 2 millimeters (e.g., from about 2 millimeters to about 50 millimeters), greater than about 5 millimeters (e.g., from about 5 millimeters to about 50 millimeters), greater than about 10 millimeters (e.g., from about 10 millimeters to about 50 millimeters), greater than another suitable threshold or within another suitable range. Suitable materials and material classes for the liquid-absorbing element 106 include, for example, porous media (e.g., fabrics and open-cell foams), polymers (e.g., polyvinyl alcohol), hydrophilic polymers, and desiccants, among others. In some embodiments, the liquid-absorbing element 106 is capable of absorbing at least about five times (e.g., from about 5 times to about 100 times) its weight in liquid water, such as at least about 10 times (e.g., from about 10 times to about 100 times) its weight in liquid water. In other embodiments, the liquid-absorbing element 106 can have other suitable absorbent properties. Furthermore, the liquid-absorbing element 106 can include an antimicrobial agent (e.g., colloidal silver), which can add another layer of protection against infection.

Figure 4:
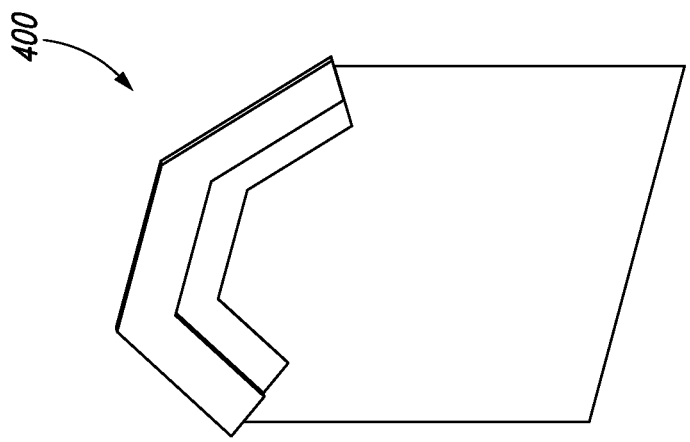
FIGS. 2-4 are perspective views illustrating protective devices similar to the protective device of FIGS. 1A-1D, but having different suitable peripheral coverage of adhesive films and liquid-absorbing elements configured in accordance with embodiments of the present technology.
Figure 3:
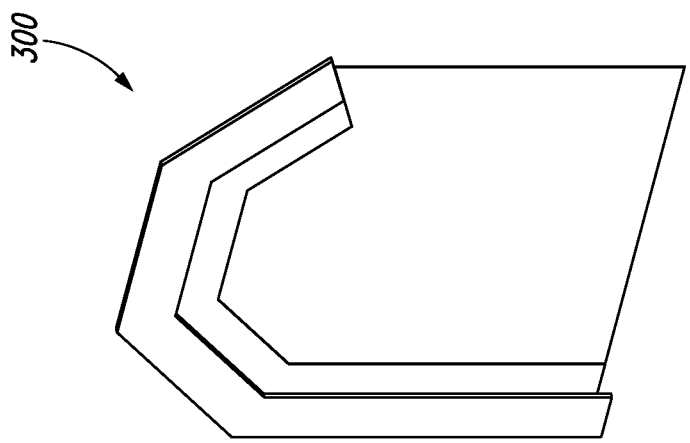
Figure 2:
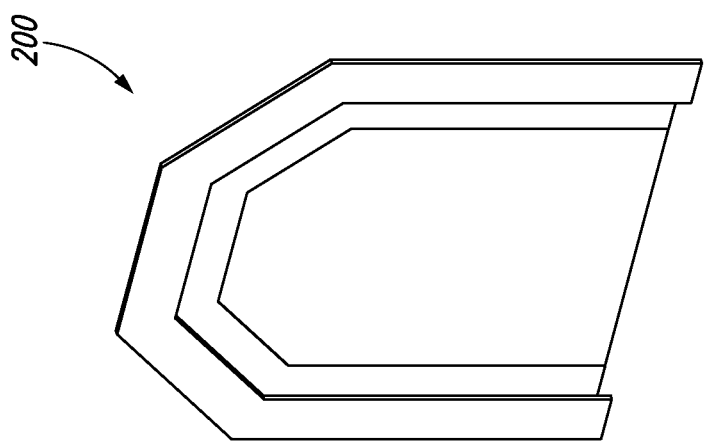
Figure 8:
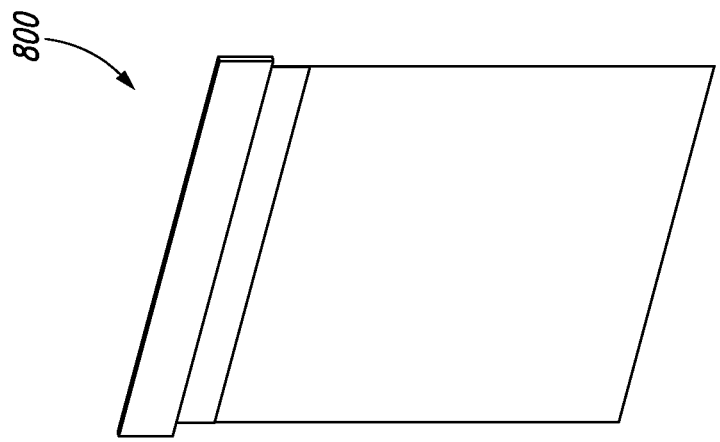
FIGS. 6-8 are perspective views illustrating protective devices similar to the protective device of FIGS. 5A-5D, but having different suitable peripheral coverage of adhesive films and liquid-absorbing elements configured in accordance with embodiments of the present technology.
Figure 7:
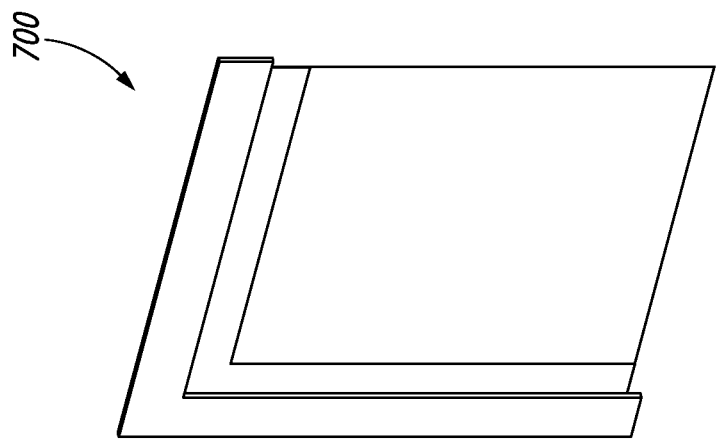
Figure 6:
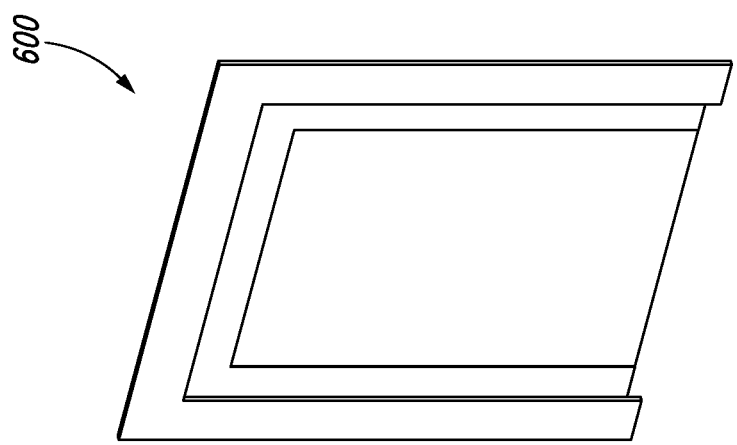
Figure 12:
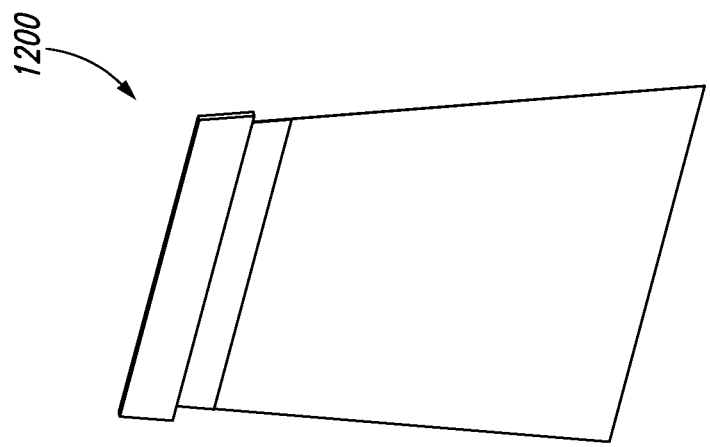
FIGS. 10-12 are perspective views illustrating protective devices similar to the protective device of FIGS. 9A-9D, but having different suitable peripheral coverage of adhesive films and liquid-absorbing elements configured in accordance with embodiments of the present technology.
Figure 11:
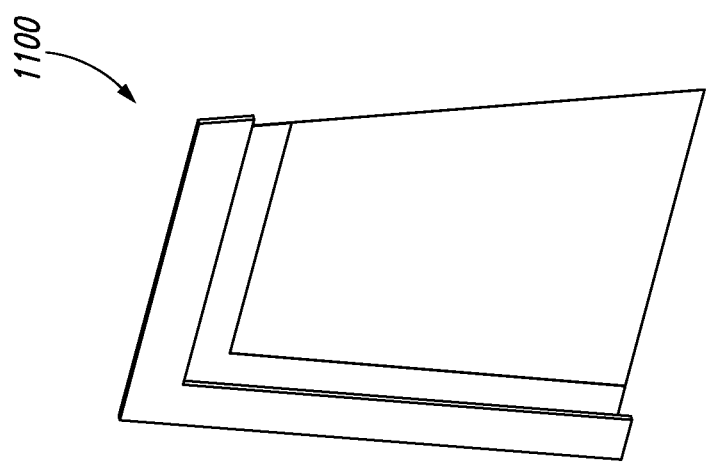
Figure 10:
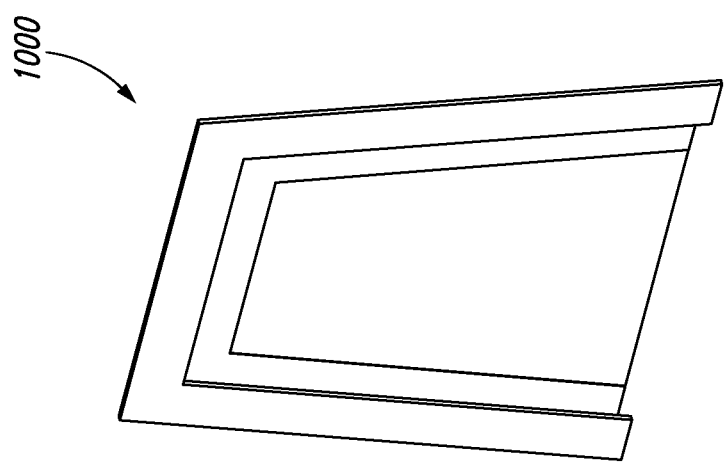

FIGS. 2, 3 and 4 are perspective views illustrating, respectively, protective devices 200, 300 and 400 that are similar to the protective device 100, but have different suitable peripheral coverage of adhesive films and liquid-absorbing elements. FIGS. 5A-5D illustrate a protective device 500 similar to the protective device 100, but having a different suitable shape. FIGS. 6, 7 and 8 are perspective views illustrating, respectively, protective devices 600, 700 and 800 that are similar to the protective device 500, but have different suitable peripheral coverage of adhesive films and liquid-absorbing elements. FIGS. 9A-9D illustrate a protective device 900 similar to the protective device 100, but having a different suitable shape. FIGS. 10, 11 and 12 are perspective views illustrating, respectively, protective devices 1000, 1100 and 1200 that are similar to the protective device 900, but have different suitable peripheral coverage of adhesive films and liquid-absorbing elements. A variety of other suitable shapes and peripheral coverage are also possible. For example, different shapes can be selected based on anatomical differences among patients, different characteristics of different types of vulnerable sites to be protected, and/or different dimensions of percutaneous devices. The peripheral coverage can be selected, for example, based on these factors alone or together with different demands for ventilation and/or different demands for accessibility of vulnerable sites.

Figure 16:
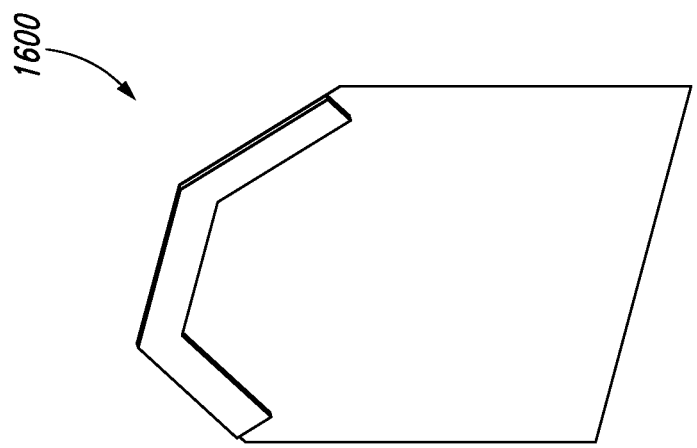
FIGS. 14-16 are perspective views illustrating protective devices similar to the protective device of FIGS. 13A-13D, but having different suitable peripheral coverage of adhesive films and liquid-absorbing elements configured in accordance with embodiments of the present technology.
Figure 15:
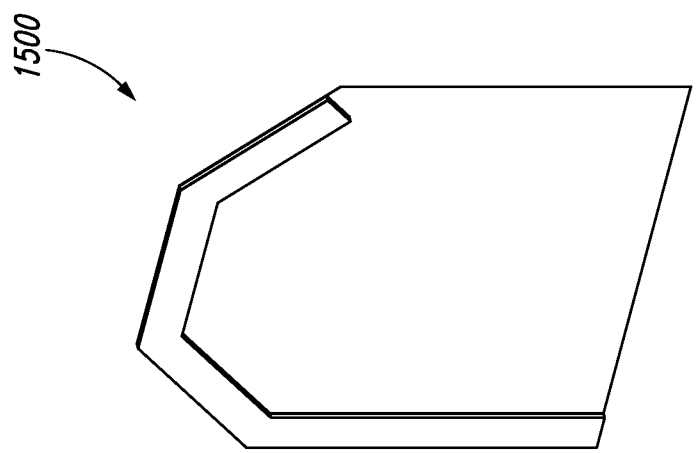
Figure 14:
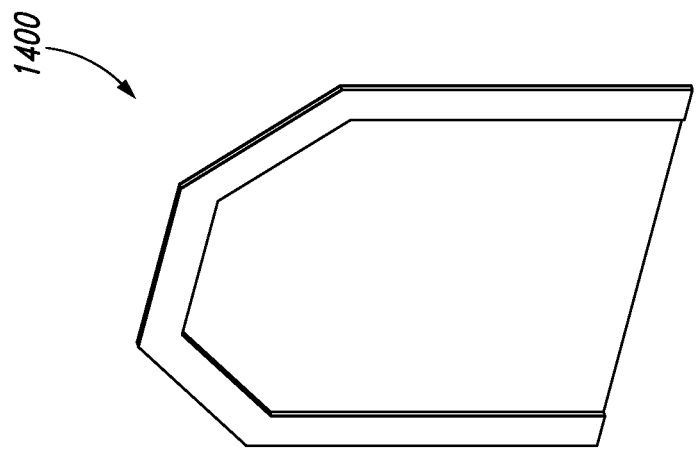
Figure 18:
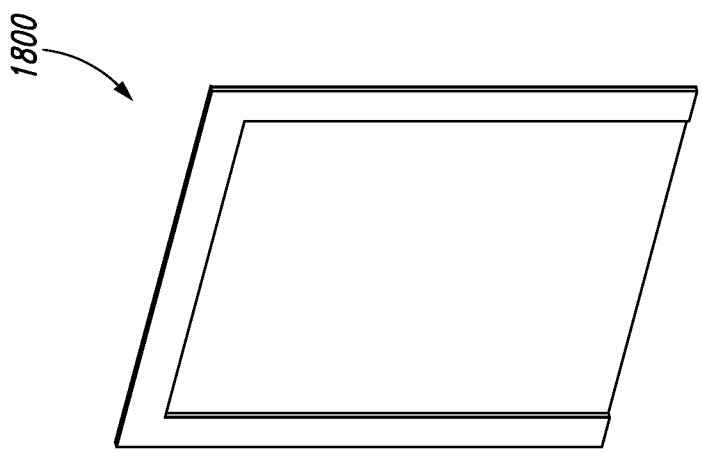
FIGS. 18-20 are perspective views illustrating protective devices similar to the protective device of FIGS. 17A-17D, but having different suitable peripheral coverage of adhesive films and liquid-absorbing elements configured in accordance with embodiments of the present technology.
Figure 19:
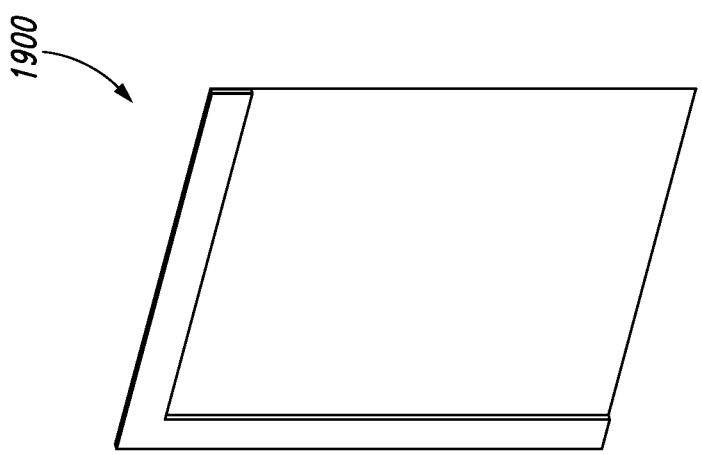
Figure 20:
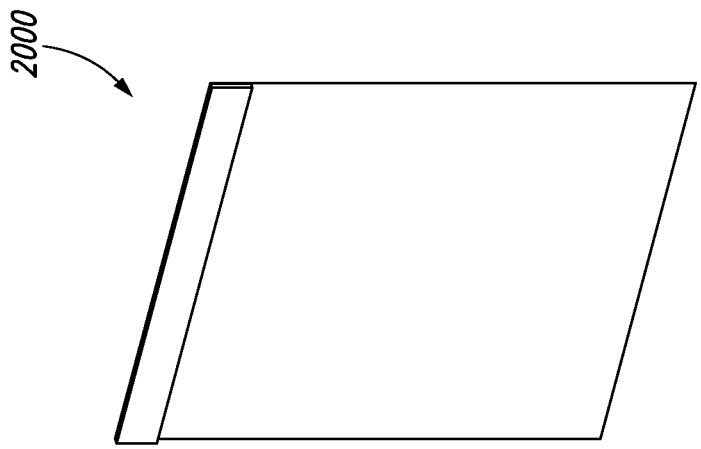
Figure 24:
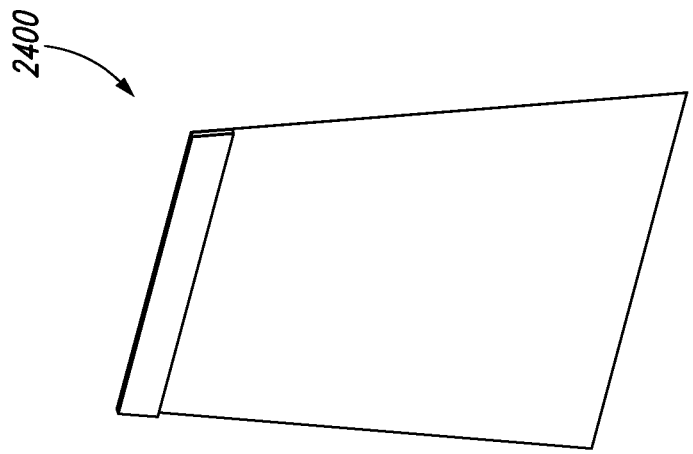
FIGS. 22-24 are perspective views illustrating protective devices similar to the protective device of FIGS. 21A-21D, but having different suitable peripheral coverage of adhesive films and liquid-absorbing elements configured in accordance with embodiments of the present technology.
Figure 23:
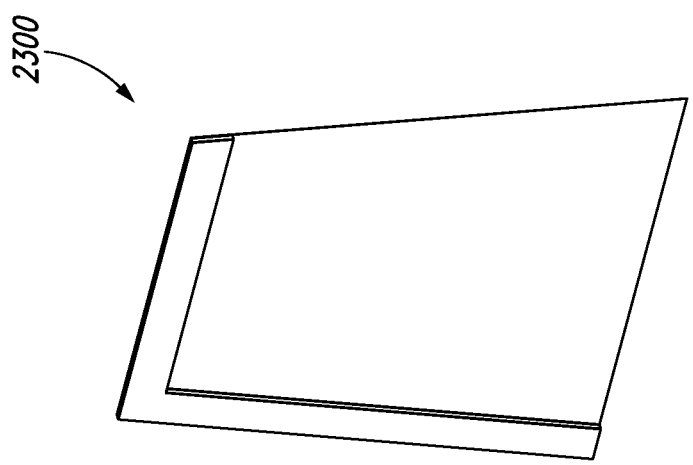
Figure 22:
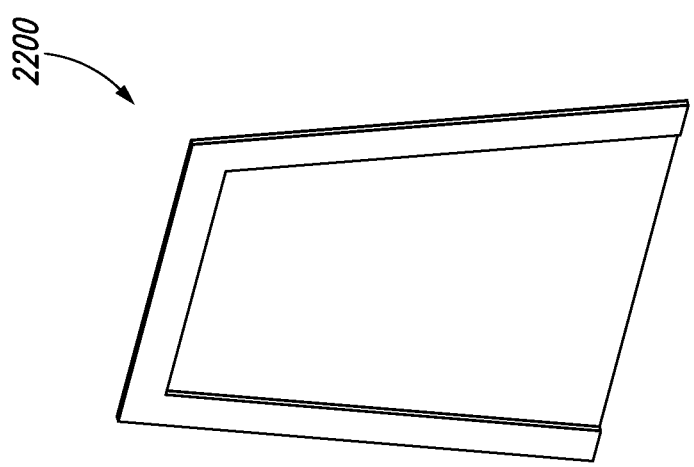

FIGS. 13A-13D illustrate a protective device 1300 similar to the protective device 100, but having a first adhesive film 1302 configured to be positioned between a liquid-absorbing element 1304 and a patient (not shown) as well as a second adhesive film 1306 positioned between the liquid-absorbing element 1304 and an associated cover. The liquid-absorbing element 1304 can have an inner edge portion 1304a toward a vulnerable site (not shown) and an outer edge portion 1304b away from the vulnerable site. FIGS. 14, 15 and 16 are perspective views illustrating, respectively, protective devices 1400, 1500 and 1600 that are similar to the protective device 1300, but have different suitable peripheral coverage of adhesive films and liquid-absorbing elements. FIGS. 17A-17D illustrate a protective device 1700 similar to the protective device 1300, but having a different suitable shape. FIGS. 18, 19 and 20 are perspective views illustrating, respectively, protective devices 1800, 1900 and 2000 that are similar to the protective device 1700, but have different suitable peripheral coverage of adhesive films and liquid-absorbing elements. FIGS. 21A-21D illustrate a protective device 2100 similar to the protective device 1300, but having a different suitable shape. FIGS. 22, 23 and 24 are perspective views illustrating, respectively, protective devices 2200, 2300 and 2400 that are similar to the protective device 2100, but have different suitable peripheral coverage of adhesive films and liquid-absorbing elements.

Figure 28:
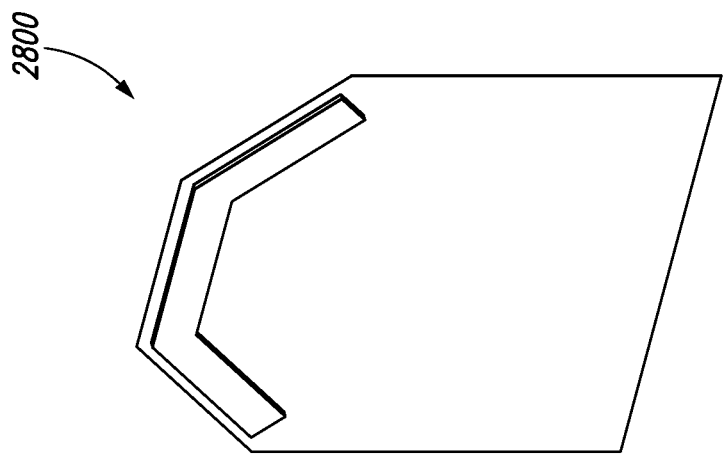
FIGS. 26-28 are perspective views illustrating protective devices similar to the protective device of FIGS. 25A-25D, but having different suitable peripheral coverage of adhesive films and liquid-absorbing elements configured in accordance with embodiments of the present technology.
Figure 27:
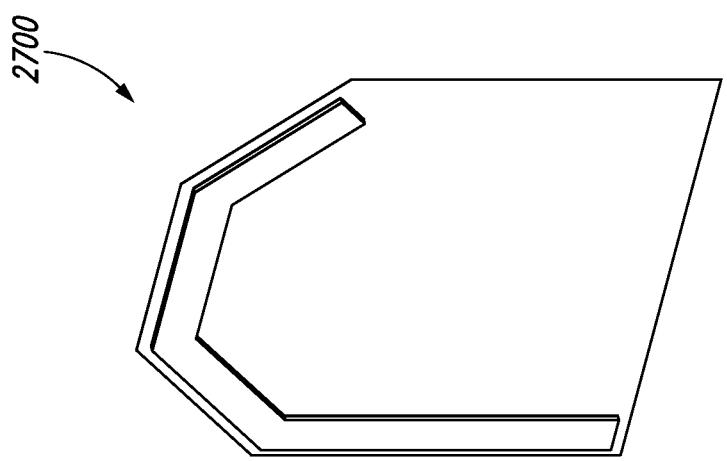
Figure 26:
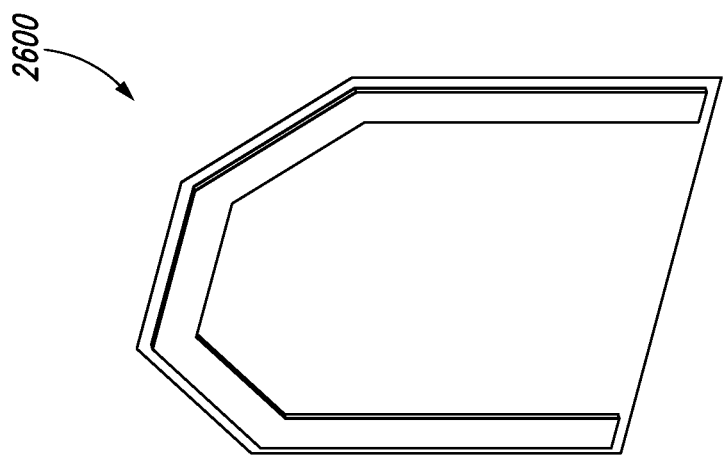
Figure 32:
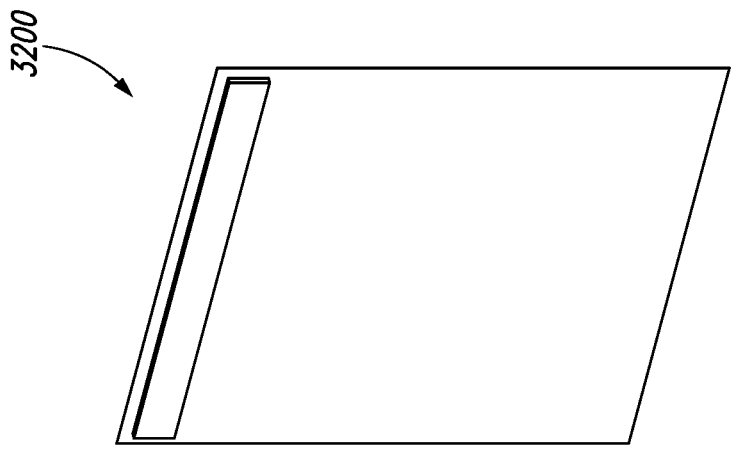
FIGS. 30-32 are perspective views illustrating protective devices similar to the protective device of FIGS. 29A-29D, but having different suitable peripheral coverage of adhesive films and liquid-absorbing elements configured in accordance with embodiments of the present technology.
Figure 31:
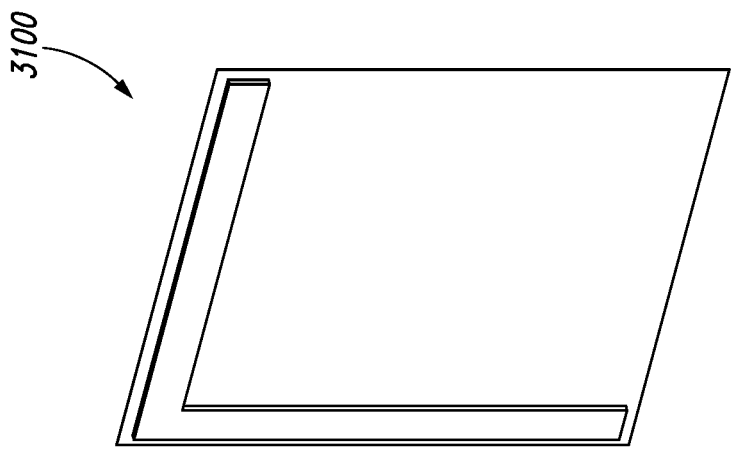
Figure 30:
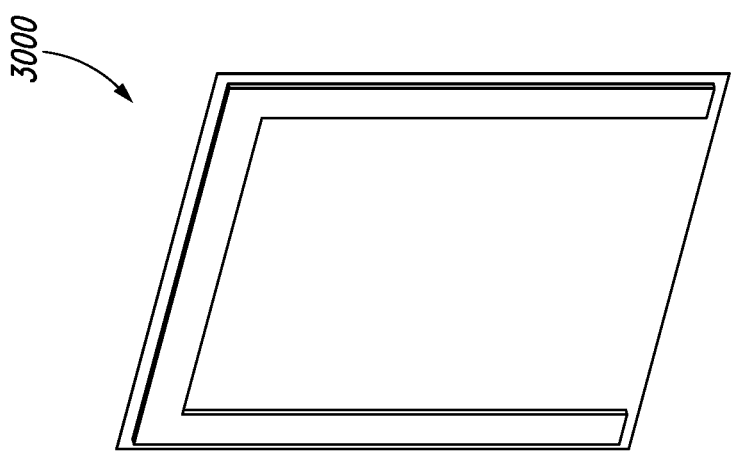
Figure 36:
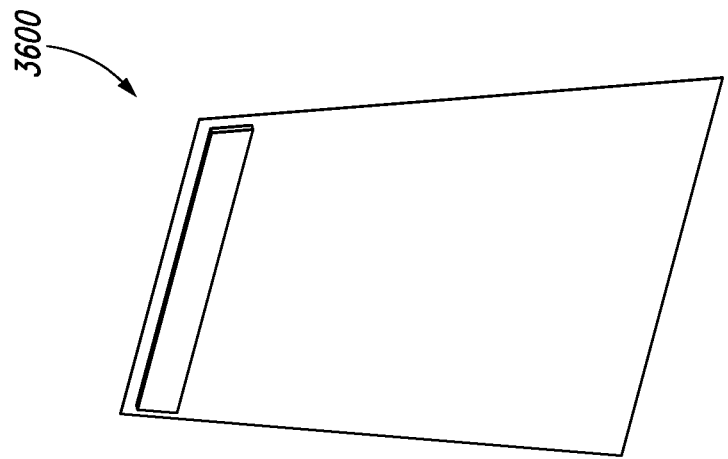
FIGS. 34-36 are perspective views illustrating protective devices similar to the protective device of FIGS. 33A-33D, but having different suitable peripheral coverage of adhesive films and liquid-absorbing elements configured in accordance with embodiments of the present technology.
Figure 35:
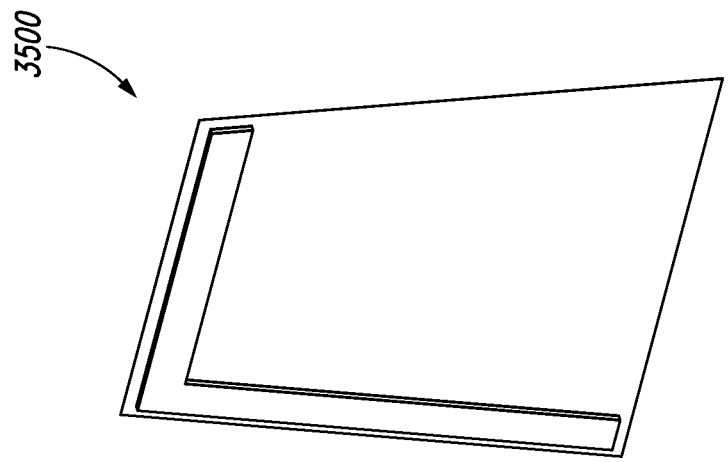
Figure 34:
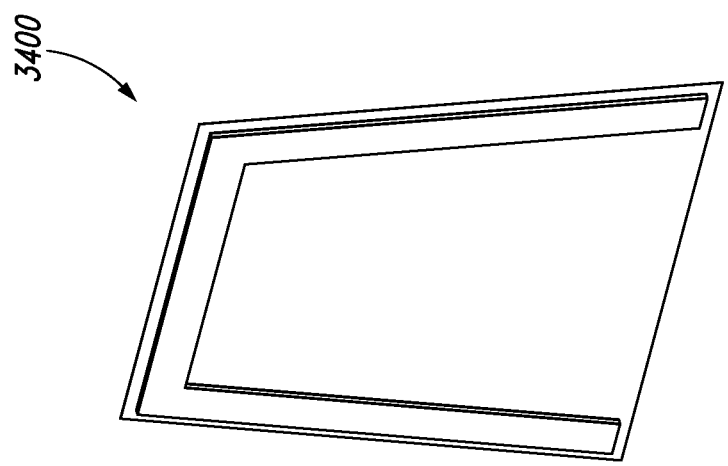

FIGS. 25A-25D illustrate a protective device 2500 similar to the protective device 1300, but having the first adhesive film 1302, the liquid-absorbing element 1304, and the second adhesive film 1306 inset relative to the outer edge portion 102e of the cover 102 such that a flap 2502 extends over the outer edge portion 1304b of the liquid-absorbing element 1304. FIGS. 26, 27 and 28 are perspective views illustrating, respectively, protective devices 2600, 2700 and 2800 that are similar to the protective device 2500, but have different suitable peripheral coverage of adhesive films and liquid-absorbing elements. FIGS. 29A-29D illustrate a protective device 2900 similar to the protective device 2500, but having a different suitable shape. FIGS. 30, 31 and 32 are perspective views illustrating, respectively, protective devices 3000, 3100 and 3200 that are similar to the protective device 2900, but have different suitable peripheral coverage of adhesive films and liquid-absorbing elements. FIGS. 33A-33D illustrate a protective device 3300 similar to the protective device 2500, but having a different suitable shape. FIGS. 34, 35 and 36 are perspective views illustrating, respectively, protective devices 3400, 3500 and 3600 that are similar to the protective device 3300, but have different suitable peripheral coverage of adhesive films and liquid-absorbing elements.

Selected Examples of Protective Methods

Figure 37:
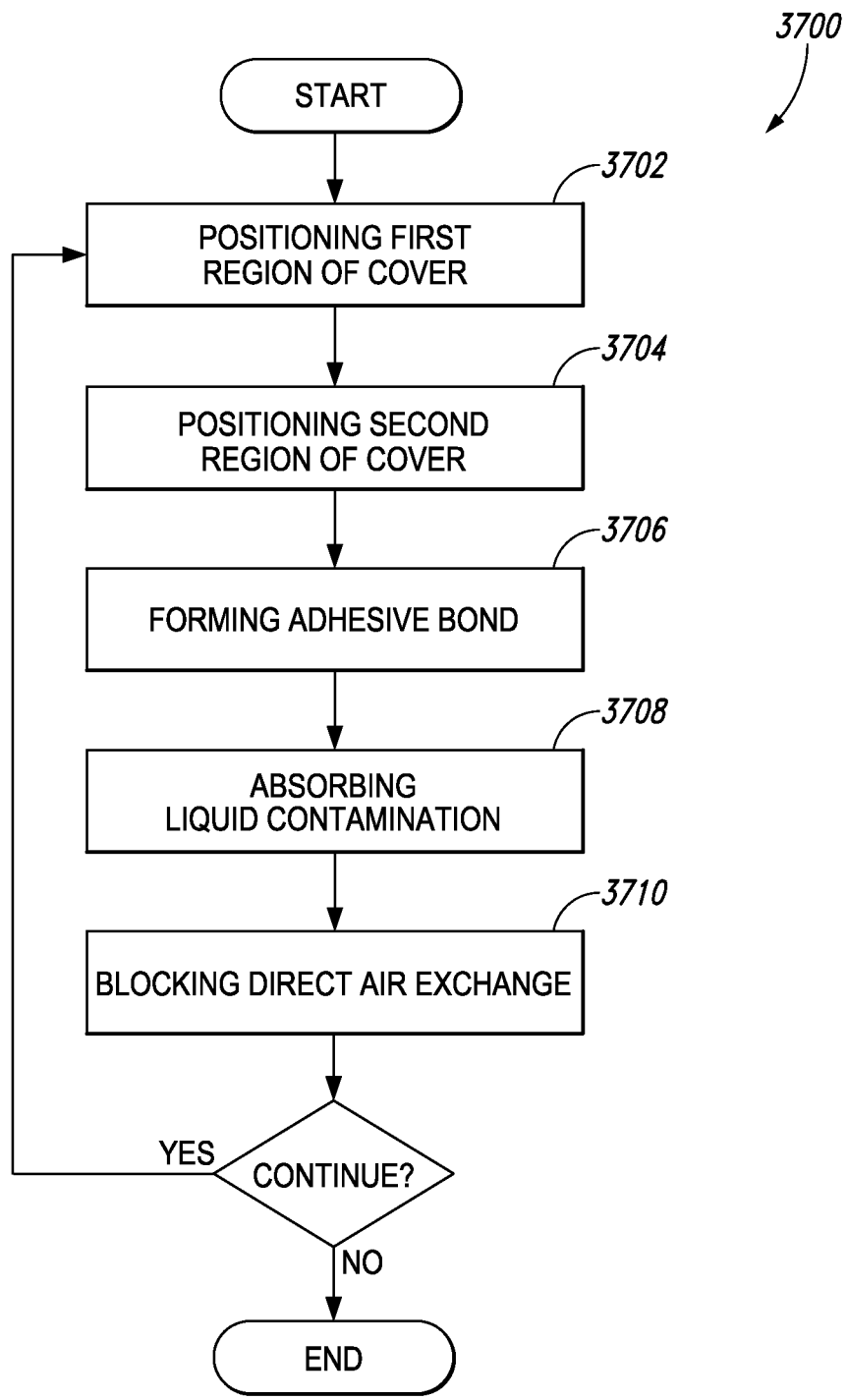
FIG. 37 is a flow chart illustrating a protective method 3700 in accordance with an embodiment of the present technology.

FIG. 37 is a flow chart illustrating a protective method 3700 in accordance with an embodiment of the present technology. With reference to FIGS. 1A-1E and 37 together, the method 3700 can include positioning the first region 102a of the cover 102 over a vulnerable site on a human patient (block 3702) and positioning the second region 102b of the cover 102 between the vulnerable site and an actual or potential source of liquid contamination (block 3704). For example, the vulnerable site can be at least proximate to the patient's neck and the second region 102b of the cover 102 can be positioned between the vulnerable site and the patient's mouth and/or nose. The method 3700 can further include forming the adhesive bond 107 between the second region 102b of the cover 102 and the patient (block 3706). In some embodiments, this includes forming the bond 107 around the entire perimeter of the first region 102a of the cover 102. In other embodiments, this can include forming the bond 107 around a suitable percentage of a perimeter of the first region 102a of the cover 102, such as from about 10% to about 90% of the perimeter of the first region 102a of the cover 102.

Next, the method 3700 can include absorbing liquid contamination (e.g., respiratory exudates from the patient's mouth and/or nose) at the outer edge portion 107b of the bond 107 and/or liquid contamination approaching the outer edge portion 107b of the bond 107 using the liquid-absorbing element 106 (block 3708). For example, the method 3700 can include wicking liquid contamination away from the outer edge portion 107b of the bond 107 and into the liquid-absorbing element 106. In some embodiments, the liquid contamination is absorbed via an outwardly projecting portion of the liquid-absorbing element 106 positioned further from the vulnerable site than the outer edge portion 107b of the bond 107. After the liquid-absorbing element 106 absorbs the liquid contamination, the method 3700 can include at least generally blocking direct exchange between air in contact with the vulnerable site at one side of the bond 107 and air in contact with liquid contamination within the liquid-absorbing element 106 at an opposite side of the bond 107 (block 3710).

The method 3700 can also include other suitable operations. As an example, the method 3700 can include loosely positioning the first region 102a of the cover 102 over a percutaneous device at the vulnerable site. In addition or alternatively, the method 3700 can include tightly positioning the first region 102a of the cover 102 over a percutaneous device at the vulnerable site, such as to at least partially secure a position of the percutaneous device relative to the patient. As another example, the method 3700 can include visually monitoring the vulnerable site through the first region 102a of the cover 102. As another example, the method 3700 can include moving the first region 102a of the cover 102 to at least partially expose the vulnerable site without disrupting the bond 107. As another example, the method 3700 can include at least generally blocking direct contact between liquid contamination within the liquid-absorbing element 106 at one side of the cover 102 and the patient at an opposite side of the cover 102, such as when the liquid-absorbing element 106 is disposed along the second side 102d of the second region 102b of the cover 102. As another example, the method 3700 can include ventilating the vulnerable site through a gap between the patient and a third region of the cover 102 at a portion of the perimeter of the first region 102a of the cover 102 around which the bond 107 is not formed.

Conclusion

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown or described in detail to avoid unnecessarily obscuring the description of embodiments of the present technology. Although steps of methods may be presented herein in a particular order, in alternative embodiments the steps may have other suitable orders. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown or described herein.

The methods disclosed herein include and encompass, in addition to methods of practicing the present technology (e.g., methods of making and using the disclosed devices and systems), methods of instructing others to practice the present technology. For example, a method in accordance with a particular embodiment includes positioning a first region of a cover over a vulnerable site on a human patient, positioning a second region of the cover between the vulnerable site and an actual or potential source of liquid contamination, forming an adhesive bond between the second region of the cover and the patient, absorbing liquid contamination at an outer edge portion of the bond and/or liquid contamination approaching the outer edge portion of the bond using a liquid-absorbing element attached to the cover, and at least generally blocking direct exchange between air in contact with the vulnerable site at one side of the bond and air in contact with liquid contamination within the liquid-absorbing element at an opposite side of the bond. A method in accordance with another embodiment includes instructing such a method.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

We claim:

1. A protective method, comprising:
    positioning a first region of a cover over a vulnerable site on a human patient, the first region of the cover being at least generally impermeable to liquid water;
    positioning a second region of the cover between the vulnerable site and the patient's mouth and/or nose;
    forming an adhesive bond between the second region of the cover and the patient, the bond having an inner edge portion positioned toward the vulnerable site and an outer edge portion positioned away from the vulnerable site;
    absorbing respiratory exudates from the patient's mouth and/or nose at the outer edge portion of the bond and/or respiratory exudates approaching the outer edge portion of the bond using a liquid-absorbing element attached to the cover; and
    at least generally blocking direct exchange between air in contact with the vulnerable site at one side of the bond and air in contact with respiratory exudates within the liquid-absorbing element at an opposite side of the bond.

2. The protective method of claim 1 wherein positioning the first region of the cover over the vulnerable site includes positioning the first region of the cover over a vulnerable site at least proximate to the patient's neck.

3. The protective method of claim 1 wherein positioning the first region of the cover over the vulnerable site includes positioning the first region of the cover over a percutaneous device at the vulnerable site.

4. The protective method of claim 1, further comprising moving the first region of the cover to at least partially expose the vulnerable site without disrupting the bond.

5. The protective method of claim 1, further comprising visually monitoring the vulnerable site through the first region of the cover.

6. The protective method of claim 1 wherein:
   forming the bond includes forming the bond around from about 10% to about 90% of a perimeter of the first region of the cover; and
   the method further comprises ventilating the vulnerable site through a gap between the patient and a third region of the cover at a portion of the perimeter of the first region of the cover around which the bond is not formed.

7. The protective method of claim 1 wherein absorbing respiratory exudates includes wicking respiratory exudates away from the outer edge portion of the bond.

\* \* \* \* \*